(12) United States Patent
Zhu et al.

(10) Patent No.: US 12,307,348 B2
(45) Date of Patent: May 20, 2025

(54) NEURAL NETWORK MODEL AND ULTRASONIC BEAM FORMING METHOD BASED ON NEURAL NETWORK MODEL

(71) Applicant: SHANGAI SOUNDWISE TECHNOLOGY CO., LTD, Shanghai (CN)

(72) Inventors: Ruixing Zhu, Shanghai (CN); Jing Zhao, Shanghai (CN); Weina Jiang, Shanghai (CN); Yunyan Zhang, Shanghai (CN); Jianqiao Zhou, Shanghai (CN)

(*) Notice: Subject to any disclaimer, the term of this patent is extended or adjusted under 35 U.S.C. 154(b) by 944 days.

(21) Appl. No.: 17/145,805

(22) Filed: Jan. 11, 2021

(65) Prior Publication Data
US 2021/0224631 A1 Jul. 22, 2021

(30) Foreign Application Priority Data
Jan. 20, 2020 (CN) .......................... 202010061972.7

(51) Int. Cl.
*G06N 3/04* (2023.01)
*G06T 5/00* (2024.01)
(52) U.S. Cl.
CPC ................ *G06N 3/04* (2013.01); *G06T 5/00* (2013.01); *G06T 2207/10024* (2013.01); *G06T 2207/10132* (2013.01); *G06T 2207/20084* (2013.01)
(58) Field of Classification Search
CPC . G06N 3/04; G06N 3/045; G06T 5/00; G06T 11/00; G06T 2207/10024; G06T 2207/10132; G06T 2207/20084; G06T 5/92; A61B 8/00; A61B 8/08; A61B 8/54; A61B 8/5207; G01S 15/50; G01S 15/8979; G01S 7/52; G01S 7/52026
See application file for complete search history.

(56) References Cited

U.S. PATENT DOCUMENTS

| | | | |
|---|---|---|---|
| 6,416,476 B1 * | 7/2002 | Ogasawara | G01S 7/52084 600/443 |
| 11,151,416 B2 * | 10/2021 | Chuang | G06F 18/2148 |
| 11,170,301 B2 * | 11/2021 | Zhang | G06N 3/082 |
| 11,300,645 B2 * | 4/2022 | Schlemper | G06V 10/768 |
| 11,324,485 B2 * | 5/2022 | Hope Simpson | G01S 7/52036 |

(Continued)

*Primary Examiner* — Stephen R Koziol
*Assistant Examiner* — Benedict E Lee
(74) *Attorney, Agent, or Firm* — Nwamu IP Law, LLC (57) ABSTRACT

The invention provides an ultrasonic beam forming method based on a neural network model. The method comprises: receiving, by the processing device, the ultrasonic echo radio frequency signal, and performing a preliminary processing of the ultrasonic echo radio frequency signal, so that the ultrasonic echo radio frequency signal is applicable to the neural network model; inputting the ultrasonic echo radio frequency signal into the neural network model; performing a convolution processing on the ultrasonic echo radio frequency signal for multiple times, and performing pooling processing after each convolution processing; flattening the ultrasonic echo radio frequency signal after the last pooling process is completed, so as to convert the ultrasonic echo radio frequency signal from three-dimensional data into one-dimensional data; classifying the one-dimensional data for multiple times; and performing grayscale mapping on the classified ultrasonic echo radio frequency signal to form an ultrasonic beam.

9 Claims, 3 Drawing Sheets

(56) References Cited

U.S. PATENT DOCUMENTS

| | | | |
|---|---|---|---|
| 11,675,066 B2* | 6/2023 | Chen | G01S 13/003 |
| | | | 342/28 |
| 2018/0330518 A1* | 11/2018 | Choi | A61B 8/0883 |
| 2019/0036108 A1* | 1/2019 | Jiao | H01M 4/587 |
| 2019/0355093 A1* | 11/2019 | Ye | G06T 5/70 |
| 2020/0226748 A1* | 7/2020 | Kaufman | G06V 10/809 |
| 2021/0038321 A1* | 2/2021 | Toporek | G06V 10/764 |
| 2021/0113191 A1* | 4/2021 | Zou | A61B 8/483 |
| 2021/0192323 A1* | 6/2021 | Whatmough | G06N 3/045 |
| 2021/0265042 A1* | 8/2021 | Kim | A61B 8/5246 |
| 2021/0279880 A1* | 9/2021 | Giner | G06T 7/168 |
| 2021/0382157 A1* | 12/2021 | Luijten | G06N 3/08 |
| 2022/0067479 A1* | 3/2022 | Lee | G06V 20/59 |

* cited by examiner

NEURAL NETWORK MODEL AND ULTRASONIC BEAM FORMING METHOD BASED ON NEURAL NETWORK MODEL

BACKGROUND OF THE INVENTION

1. Field of the Invention

The invention relates to the technical field of ultrasonic detection, and more particularly, to an ultrasonic beam forming method based on the neural network model.

2. Description of the Related Art

The conventional ultrasonic beam forming method is to receive an ultrasonic echo radio frequency signal (hereinafter referred to as RF signal), and the received RF signal is subjected to delay superposition. The method mainly comprises: after receiving the RF signal, performing a series of steps, such as, low noise amplification, variable gain amplification, low-pass filtering, analog-to-digital conversion, quadrature demodulation, envelop calculation, delay superposition, and finally, forming the ultrasonic beam.

In the prior art, the conventional ultrasonic beam forming method has some problems, that is, (1) the calculation is complex, and sound velocity is usually considered as constant value, which in turn leads to an incorrect spatial alignment of the RF signal; (2) when performing the delay superposition, some problems may arise, such as wide main lobe, high-energy side lobe, thus, the lateral resolution is reduced and the contrast is lowered; (3) in this method, calculation is done manually, and before performing calculations, the current array shape and media characteristics must be available, and the scanning sequence and the weight of each transmitting oscillating elements needs to be carefully designed, all of which impose high requirements on developers in terms of technical skills; (4) after the formation of a corresponding ultrasonic beam, image enhancement and optimization is additionally needed for the traditional ultrasonic system, and such an operation completely depends on back-end software.

Thus, the present invention provides a new ultrasonic beam forming method based on a neural network model as an alternative to the traditional method. In this method, after the RF signal is received, the RF signal enters the neural network model for optimization processing. Target feature are extracted from convolution process and pooling processes, so that an ultrasonic beam with better quality is obtained. In addition, by using the method, the calculation complexity is reduced, the development difficulty is also reduced, and costs for research & development is decreased.

SUMMARY OF THE INVENTION

Given that the foregoing problems exist in the prior art, the present invention provides a neural network model and a ultrasonic beam forming method based on the neural network model.

The detailed technical solution is as follows:

The invention comprises a ultrasonic beam forming method based on a neural network model. The method is applicable to the signal processing during ultrasonic scanning, a processing device is connected to a receiver which is configured to receive ultrasonic echo radio frequency signal, wherein the ultrasonic echo radio frequency signal is processed by the neural network model so that the ultrasonic echo radio frequency signal forms an ultrasonic beam, the neural network model is built in the processing device, wherein the method further comprises the steps of:

Step S1, receiving, by the processing device, the ultrasonic echo radio frequency signal, and performing a preliminary processing of the ultrasonic echo radio frequency signal, so that the ultrasonic echo radio frequency signal is applicable to the neural network model;

Step S2, inputting, by the processing device, the ultrasonic echo radio frequency signal which has been subjected to the preliminary processing, into the neural network model;

Step S3, performing, by the neural network model, a convolution processing on the ultrasonic echo radio frequency signal which has been subjected to the preliminary processing for multiple times, and performing pooling processing after each convolution processing;

Step S4, flattening, by the neural network model, the three-dimensional data obtained from the last pooling processing, so as to convert the three-dimensional data into one-dimensional data;

Step S5, classifying, by the neural network model, the one-dimensional data for multiple times; and Step S6, performing, by the neural network model, grayscale mapping on the classified data to form the ultrasonic beam.

Preferably, Step S1 comprises:

Step S11, classifying the ultrasonic echo radio frequency signal based on the dimensional size thereof; and Step S12, converting one-dimensional grayscale image data obtained in Step S11 into three-dimensional color image data, and going to Step S2 thereafter.

Preferably, Step S3 comprises:

Step S31, performing a first convolution processing on the ultrasonic echo radio frequency signal, and outputting the ultrasonic echo radio frequency signal through a first activation function after the first convolution processing is completed, to perform a first pooling processing;

Step S32, performing a second convolution processing on the ultrasonic echo radio frequency signal which has been subjected to the first pooling processing, and outputting the ultrasonic echo radio frequency signal through a second activation function after the second convolution processing is completed, to perform a second pooling processing;

Step S33, performing a third convolution processing on the ultrasonic echo radio frequency signal which has been subjected to the second pooling processing, and outputting the ultrasonic echo radio frequency signal through a third activation function after the third convolution is completed, to perform a third pooling operation;

Step S34, performing a fourth convolution processing on the ultrasonic echo radio frequency signal which has been subjected to the third pooling processing, and outputting the ultrasonic echo radio frequency signal through a fourth activation function after the fourth convolution processing is completed, to perform a fourth pooling processing; and Step S35, performing a fifth convolution processing on the ultrasonic echo radio frequency signal which has been subjected to the fourth pooling processing, and outputting the ultrasonic echo radio frequency signal through a fifth activation function after the fifth convolution processing is completed, to perform a fifth pooling processing.

Preferably, in Step S31, the first pooling processing is carried out by using a maximization processing method.

Preferably, all of the second pooling operation, the third pooling operation, the fourth pooling operation, and the fifth pooling operation are carried out by using an equalization processing method.

Preferably, Step S5 comprises:

Step S51, performing a first-level classification processing on the one-dimensional data, and outputting the classified one-dimensional data through a sixth activation function; and Step S52, performing a second-level classification processing on the output data obtained in Step S51, and outputting the classified output data through a seventh activation function.

Preferably, the first activation function, the second activation function, the third activation function, the fourth activation function, the fifth activation function, and the sixth activation function are RELU functions, and the seventh activation function is a Softmax function.

The invention further comprises a neural network model, applied to the method for forming the ultrasonic beam, the method comprising:

an input layer for receiving the ultrasonic echo radio frequency signal;

a plurality of convolutional layers, wherein the first-level convolutional layer is connected to the input layer;

a plurality of pooling layers, wherein each of the plurality of pooling layers is connected to a corresponding convolutional layer, each convolution processing is followed by a pooling processing;

a smoothing layer, connected to the last-level pooling layer, flattening the three-dimensional data which has been subjected to the last pooling processing, so as to convert the tree-dimensional data into one-dimensional data;

a plurality of fully connected layers, the first-level fully connected layer is connected to the smoothing layer to classify the one-dimensional data for multiple times, and performing grayscale mapping on the classified data to form the ultrasonic beam.

Preferably, the plurality of convolutional layers comprise five convolutional layers, the plurality of pooling layers comprise five pooling layers, data obtained from a first convolutional layer is processed by a first activation function and is output to a first pooling layer for performing a maximization pooling; data obtained from the first pooling layer enters a second convolutional layer, data obtained from the second convolutional layer is processed by a second activation function and is output to a second pooling layer for performing equalization pooling, data obtained from the second pooling layer enters a third convolutional layer, data obtained from the third convolutional layer is processed by a third activation function and is output to a third pooling layer for performing equalization pooling, data obtained from the third pooling layer enters a fourth convolutional layer, data obtained from the fourth convolutional layer is processed by a fourth activation function and is output to a fourth pooling layer for performing equalization pooling, data obtained from the fourth pooling layer enters a fifth convolutional layer, and data obtained from the fifth convolutional layer is processed by a fifth activation function and is output to a fifth pooling layer for performing equalization pooling.

Preferably, the plurality of fully connected layers comprise two fully connected layers, including a first fully connected layer and a second fully connected layer, wherein the first fully connected layer perform a first compression and classification processing on the one-dimensional data, the compressed and classified one-dimensional data is output to the second fully connected layer through a sixth activation function, then the second fully connected layer performs a second compression and classification processing on the output data, the output of the second fully connected layer is processed by a seventh activation function and then output.

By adopting the above-mentioned technical solutions, the present invention has the beneficial effects that the present invention provides a ultrasonic beam forming method by using a neural network model. In this method, after the RF signal is received, the RF signal enters the neural network model for optimization processing. Target feature are extracted from convolution processing and pooling processing, so that an ultrasonic beam with better quality is obtained. In addition, by using the method, the calculation complexity is reduced, the development difficulty is also reduced, and costs for research & development is decreased.

BRIEF DESCRIPTION OF THE DRAWINGS

The accompanying drawings, together with the specification, illustrate exemplary embodiments of the present disclosure, and, together with the description, serve to explain the principles of the present invention.

DETAILED DESCRIPTION

The technical solution set forth in the embodiments of the present invention will now be described clearly and fully hereinafter with reference to the accompanying drawings of the embodiments of the present invention. Obviously, such embodiments provided in the present invention are only part of the embodiments instead of all embodiments. It should be understood that all the other embodiments obtained from the embodiments set forth in the present invention by one skilled in the art without any creative work fall within the scope of the present invention.

Notably, the embodiments set forth in the present invention and features of the embodiments may be combined in any suitable manner.

The present invention will be described hereinafter with reference to the accompanying drawings and particular embodiments, but the invention is not limited thereto.

Figure 1:
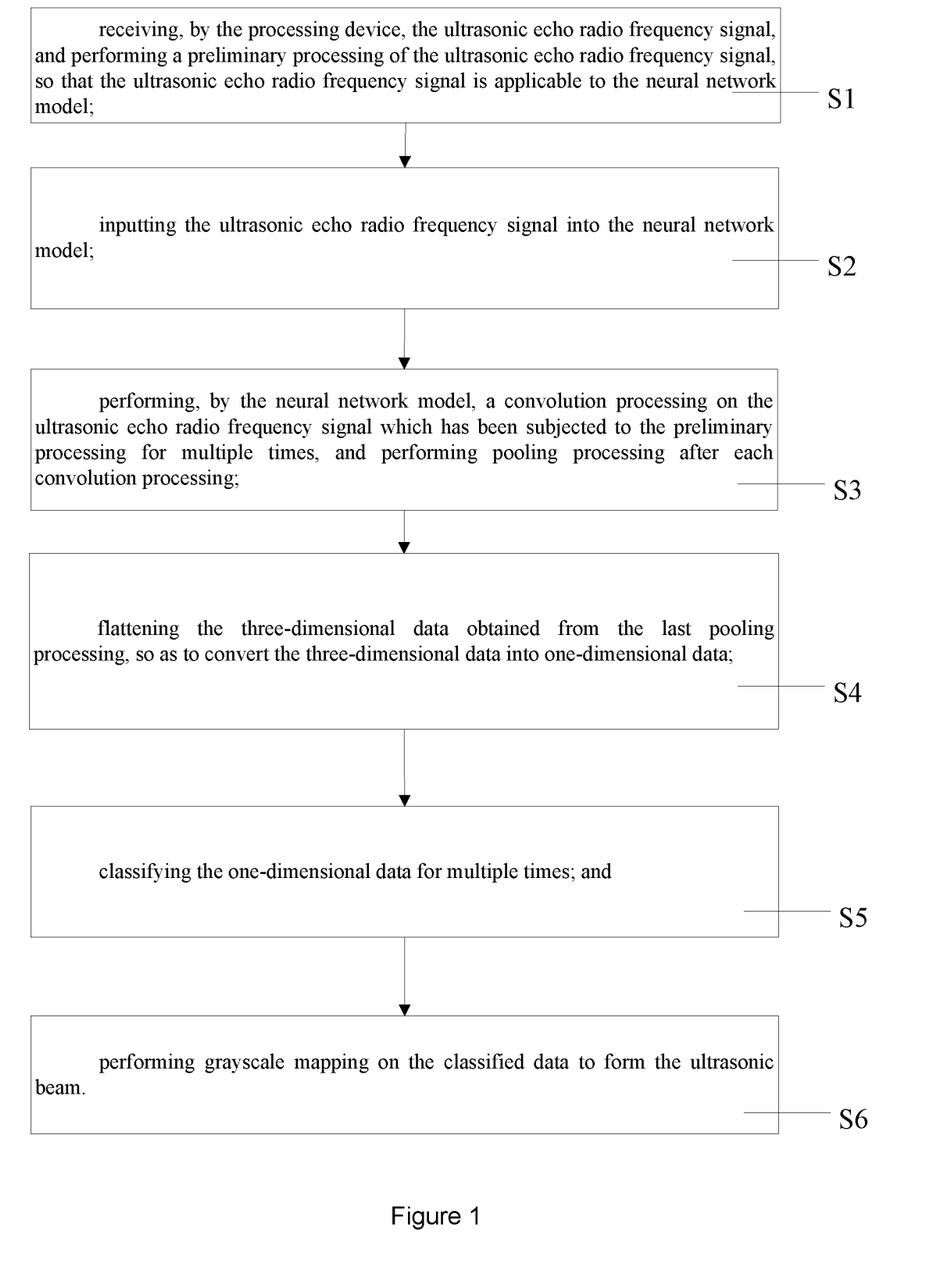
FIG. 1 is a flowchart illustrating steps of a ultrasonic beam forming method according to an embodiment of the present invention.

The invention comprises a ultrasonic beam forming method based on a neural network model. The method is applicable to the signal processing during ultrasonic scanning, a processing device is connected to a receiver which is configured to receive ultrasonic echo radio frequency signal, wherein the ultrasonic echo radio frequency signal is processed by the neural network model so that the ultrasonic echo radio frequency signal forms an ultrasonic beam, as shown in FIG. 1, the neural network model is built in the processing device, wherein the method further comprises the steps of:

Step S1, receiving, by the processing device, the ultrasonic echo radio frequency signal, and performing a preliminary processing of the ultrasonic echo radio frequency signal, so that the ultrasonic echo radio frequency signal is applicable to the neural network model;

Step S2, inputting, by the processing device, the ultrasonic echo radio frequency signal which has been subjected to the preliminary processing, into the neural network model;

Step S3, performing, by the neural network model, a convolution processing on the ultrasonic echo radio frequency signal which has been subjected to the preliminary processing for multiple times, and performing pooling processing after each convolution processing;

Step S4, flattening, by the neural network model, the three-dimensional data obtained from the last pooling processing, so as to convert the three-dimensional data into one-dimensional data;

Step S5, classifying, by the neural network model, the one-dimensional data for multiple times; and Step S6, performing, by the neural network model, grayscale mapping on the classified ultrasonic echo radio frequency signal to form the ultrasonic beam.

In particular, in this embodiment, an ultrasonic probe emits an ultrasonic radio frequency signal. The receiver periodically collects an ultrasonic echo radio frequency signal (hereinafter referred to as the RF signal) and transmits the same to a processing device. The receiver is preferably an analog-digital sampler. The processing device is a computer. The analog-digital sampler converts the RF signal from an analog signal into a digital signal which can be identified by the computer, then the RF signal converted into the digital signal is input into the computer. After receiving the RF signal, the computer performs preliminary processing on the received RF signal. For example, due to its large volume of data, the data can be processed in blocks through the preliminary processing of the RF signal, so that its size can fit the neural network model.

In particular, after the preliminary processing of the RF signal, the RF signal is sent to the neural network model for optimization. In this embodiment, the neural network model comprises an input layer, a plurality of convolutional layers, a plurality of pooling layers, a smoothing layer, and a plurality of fully connected layers. The RF signal is subjected to convolution processing and pooling processing for multiple times in the neural network model to extract target features. Classify the target features extracted from all the convolutional layers through the fully connected layers. Finally, the ultrasonic beam is formed by grayscale mapping, and an ultrasound image is synthesized through the ultrasonic beam. The above-mentioned method can replace the traditional delay superposition method. The method proposed in the present invention makes it possible to reduce the difficulty in developing the ultrasonic system and to reduce the complexity of calculation, so that the ultrasonic system is capable of forming images more quickly, and higher ultrasonic image quality is obtained.

Figure 2:
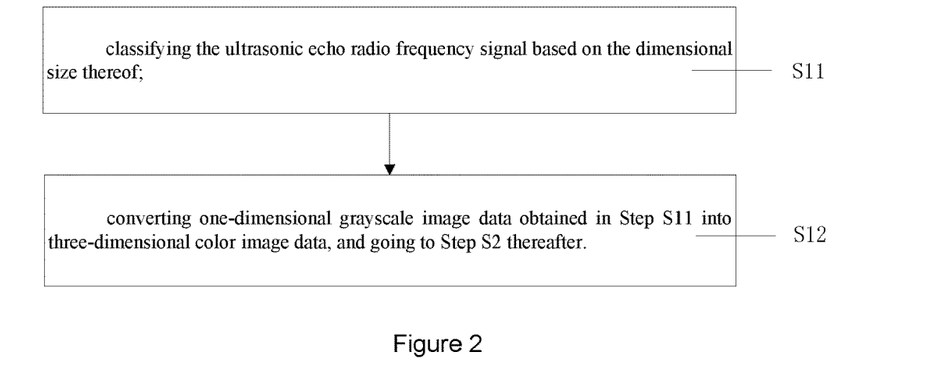
FIG. 2 is a flowchart illustrating sub-steps of Step S1 according to an embodiment of the present invention.

In a preferred embodiment, as shown in FIG. 2, Step S1 comprises:

Step S11, classifying the ultrasonic echo radio frequency signal based on the dimensional size thereof; and Step S12, converting the ultrasonic echo radio frequency signal from grayscale image data to color image data, and going to Step S2 thereafter.

In particular, in this embodiment, the preliminary processing comprises two main steps. The first step is to perform data block processing on the RF signal so that the size of the data can adapt to the processing procedure of the neural network model. In this embodiment, the data is organized into blocks according to the dimensional size of 244*244. In addition, the dimension of the data needs to be changed. The original RF signal is one-dimensional grayscale image data. The opencv method is used to convert the grayscale image data into three-dimensional color image data (hereinafter referred to as RGB data) to facilitate subsequent formation of color ultrasound images.

In particular, for RGB data, each of the RGB component can use a value ranging from 0 (black) to 255 (white). For example, a bright red color may have an R value of 246, a G value of 20, and a B value of 50. When the values of all the three components are equal, the result is a shade of gray. When the values of all components are 255, the result is pure white. When the values of all components are 0, the result is pure black. In this embodiment, in order to convert the grayscale image data into the RGB data, the values of all the three components should be made to be equal, that is, R=G=B.

Figure 3:
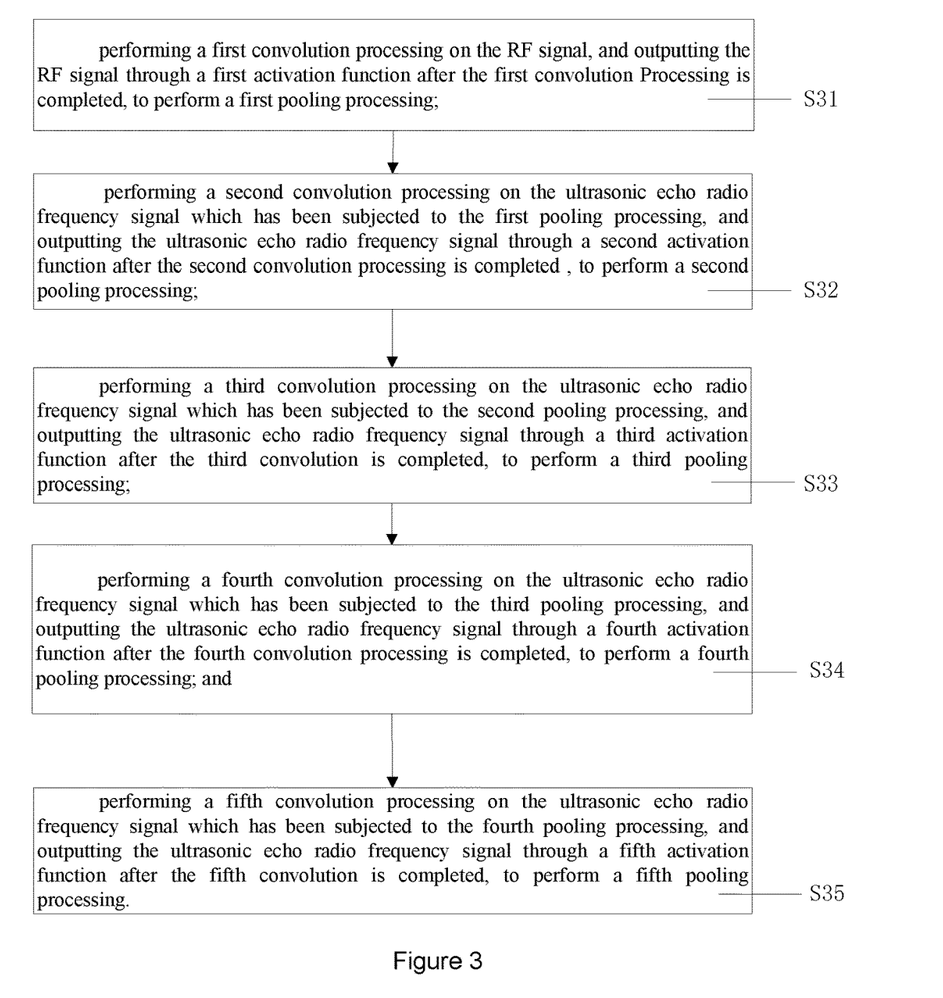
FIG. 3 is a flowchart illustrating sub-steps of Step S3 according to an embodiment of the present invention.

In a preferred embodiment, after the preliminary processing, the RF signal is input into the neural network model for five times of convolution processing and five times of pooling processing. As shown in FIG. 3, Step S3 comprises: Step S31, performing a first convolution processing on the RF signal, and outputting the RF signal through a first activation function after the first convolution processing is completed, to perform a first pooling processing; Step S32, performing a second convolution processing on the RF signal which has been subjected to the first pooling operation, and outputting the RF signal through a second activation function after the second convolution processing is completed, to perform a second pooling processing; Step S33, performing a third convolution processing on the RF signal which has been subjected to the second pooling processing, and outputting the RF signal through a third activation function after the third convolution processing is completed, to perform a third pooling processing; Step S34, performing a fourth convolution processing on the RF signal, and outputting the RF signal through a fourth activation function after the fourth convolution processing is completed, to perform a fourth pooling processing; and Step S35, performing a fifth convolution processing on the RF signal, and outputting the RF signal through a fifth activation function after the fifth convolution processing is completed, to perform a fifth pooling processing.

In particular, by adopting the above-mentioned technical solution, the RF signal first enters the first convolutional layer (B1conv1) for convolution, the filter dimension is 64, the convolution kernel of size 3×3 is used, the activation function is RELU, and the dimension size is converted from (224, 224, 3) to (224, 224, 64), the data obtained from the first convolution is output to the first pooling layer (maxPool1) through the first activation function for maximum pooling, the pooling size is 2×2, and the pooling stride is 2×2, and the dimension size is converted from (224, 224, 64) to (112, 112, 64);

the data obtained from the first pooling enters the second convolutional layer (B2conv1), the filter dimension is 128, the convolution kernel of size 3×3 is used, the dimension size is converted from (112, 112, 64) to (112, 112, 128), the data obtained from the second convolution is output to the second pooling layer (AvePool2) through the second activation function for equalization pooling, the pooling size is 2×2, and the pooling stride is 2×2, and the dimension size is converted from (112, 112, 128) to (56, 56, 128);

the data obtained from the second pooling enters the third convolutional layer (B3conv1), the filter dimension is 256, the convolution kernel of size 3×3 is used, the dimension size is converted from (56, 56, 128) to (56, 56, 256), the data obtained from the third convolution is output to the third pooling layer (AvePool3) through the third activation function for equalization pooling, the pooling size is 2×2, and the pooling stride is 2×2, and the dimension size is converted from (56, 56, 256) to (28, 28, 256);

the data obtained from the third pooling enters the fourth convolutional layer (B4conv1), the filter dimension is 512, the convolution kernel of size 3×3 is used, the dimension size is converted from (28, 28, 256) to (28, 28, 512), the data obtained from the fourth convolution is output to the fourth pooling layer (AvePool4) through the fourth activation function for equalization pooling, the pooling size is 2×2, and the pooling stride is 2×2, and the dimension size is converted from (28, 28, 512) to (14, 14, 512);

the data obtained from the fourth pooling enters the fifth convolutional layer (B5conv1), the filter dimension is 512, the convolution kernel of size 3×3 is used, the dimension size is converted from (14, 14, 512) to (14, 14, 512), the data obtained from the fifth convolution is output to the fifth pooling layer (AvePool5) through the fifth activation function for equalization pooling, the pooling size is 2×2, and the pooling stride is 2×2, and the dimension size is converted from (14, 14, 512) to (7, 7, 512);

in Step S4, flattening the data output from the fifth pooling layer, and the vector dimension is converted from (7, 7, 512) to 25088;

in step S5, the obtained one-dimensional data 25088 is sent to the first-level fully connected layer (Dense1) for first compression and classification operation. The vector dimension is converted from 25088 to 4096. The first fully connected layer output, through the six activation function, the data to the second fully connected layer for second compression and classification operation. The vector dimension is converted from 4096 to 256, and finally softmax is output through the seventh activation function, and then it turns to step S6 to perform grayscale mapping on the data output by the seventh activation function to form an ultrasonic beam.

It should be noted that the first activation function, the second activation function, the third activation function, the fourth activation function, and the fifth activation function in this embodiment are all RELU functions. The RELU function is a piecewise linear function. It turns all negative values into 0, while positive values remain the same. Such an operation is called unilateral suppression. That is to say, in case the input of the convolutional layer is a negative value, the RELU function will output 0, then the neuron will not be activated, which means that only some of neurons will be activated at the same time, making the network very sparse, which in turn makes calculations more efficient. It is due to the presence of the unilateral suppression that the neurons in the neural network also have sparse activation. As a result, target features can be better extracted, and it fits training data. The RELU function has the following advantages: saturation zone does not exist, the problem of gradient disappearance is avoided, calculation is relatively simple, and the actual convergence rate is much faster than that of the Sigmoid function and the tanh function.

In particular, after convolution processing of data is carried out at each of convolutional layers, the RELU function is activated, the data is output to the corresponding pooling layer through the RELU function for pooling processing. Feature points in small neighbors obtained after the convolutional layers are integrated to form new target features by the pooling process. On the one hand, the pooling layer can prevent useless parameters from increasing calculation time or calculation complexity, and on the other hand, it increases the integration of target features.

As a preferred embodiment, in Step 31, the first pooling process adopts the maximization processing method, while the second pooling process, the third pooling process, the fourth pooling process, and the fifth pooling process adopt the equalization processing method. The use of maximization pooling in the first pooling can ensure an original RF signal is basically reserved, and the subsequent pooling processings using the equalization processing is to make the data more smoothly transfer to a classified network.

Figure 4:
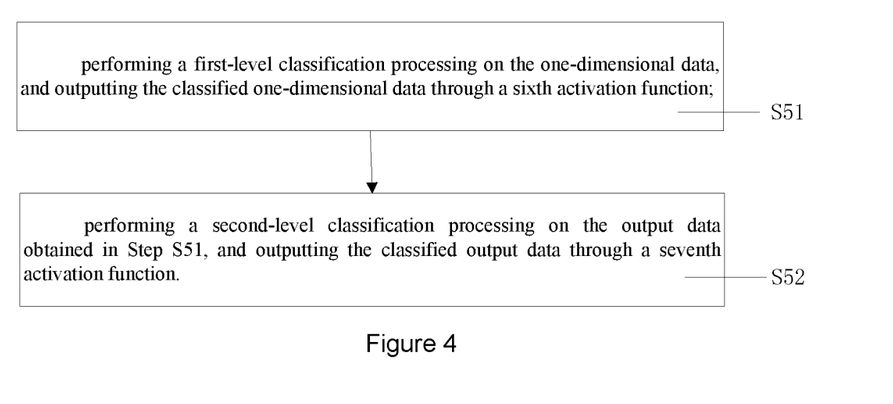
FIG. 4 is a flowchart illustrating sub-steps of Step S5 according to an embodiment of the present invention.

In a preferred embodiment, as shown in FIG. 4, Step S5 comprises:

Step S51, performing a first-level classification processing on the one-dimensional data, and outputting the classified one-dimensional data through a sixth activation function; and Step S52, performing a second-level classification processing on the output data obtained in Step S51, and outputting the classified output data through a seventh activation function.

In particular, in this embodiment, the method comprises two fully connected layers. After the three-dimensional data is flattened in Step S4, the first-level fully connected layer vector dimension is converted from (7, 7, 512) to 25088, and the data is classified and processed. The vector dimension is converted from 25088 to 4096, and is output to next-level fully connected layer through the activation function RELU. The next-level fully connected layer compresses and classifies the data again. The vector dimension is converted from 4096 to 256, and is output through the softmax function. 256 classifications formed by the classified network are distributed to the corresponding gray levels through grayscale mapping. The 256 classifications are compared with the mark content by using the one-hot encoding. Finally, the ultrasonic beam is formed after they are optimized by the neutral network model.

The invention further comprises a neural network model, applied to the ultrasonic beam forming method in the above-mentioned technical solution, as shown in table 1, the neural network model comprising:

an input layer for receiving the ultrasonic echo radio frequency signal;

a plurality of convolutional layers, wherein the first-level convolutional layer is connected to the input layer;

a plurality of pooling layers, wherein each of the plurality of pooling layers is connected to a corresponding convolutional layer;

a smoothing layer, connected to the last-level pooling layer;

a plurality of fully connected layers, the first-level fully connected layer is connected to the smoothing layer.

In particular, in this embodiment, an improved neutral network model is provided on the basis of VGG model, allowing it to be suitable for an ultrasound imaging systems. The neural network model in this embodiment comprises an input layer, five convolutional layers (B1conv1 to B5conv1 shown in Table 1), five pooling layers (maxPool1, AvePool2, AvePool3, AvePool4, AvePool5 shown in Table 1), a smoothing layer (Flatten) and two fully connected layers (Dense1 and Dense2 shown in Table 1). Compared with the existing VGG model, the neural network model has fewer convolutional layers, which makes the calculation faster, thereby increasing the speed of ultrasound imaging; in addition, the first pooling layer in this embodiment adopts maximization pooling processing. The use of maximization pooling in the first pooling can ensure an original RF signal is basically reserved, and the subsequent pooling processings using the equalization processing is to make the data more smoothly transfer to a classified network. Finally, the obtained ultrasound image is more delicate. The neural network model in this embodiment is shown in table 1.

TABLE 1

| Name of network layer | Size of convolution kernel | Filter dimension | Output size | Activation function |
|---|---|---|---|---|
| B1conv1 | 3 × 3, stride = 1 | 64 | (224, 224, 64) | RELU |
| maxPool1 | 2 × 2, stride = 2 × 2 | | (112, 122, 64) | |
| B2conv1 | 3 × 3, stride = 1 | 128 | (112, 112, 128) | RELU |
| AvePool2 | 2 × 2, stride = 2 × 2 | | (56, 56, 128) | |
| B3conv1 | 3 × 3, stride = 1 | 256 | (56, 56, 256) | RELU |
| AvePool3 | 2 × 2, stride = 2 × 2 | | (28, 28, 256) | |
| B4conv1 | 3 × 3, stride = 1 | 512 | (28, 28, 512) | RELU |
| Avepool4 | 2 × 2, stride = 2 × 2 | | (14, 14, 512) | |
| B5conv1 | 3 × 3, stride = 1 | 512 | (14, 14, 512) | RELU |
| Avepool5 | 2 × 2, stride = 2 × 2 | | (7, 7, 512) | |
| Flatten | | | 25088 | |
| Dense1 | | | 4096 | RELU |
| Dense2 | | | 256 | softmax |

By adopting the above-mentioned technical solutions, the present invention has the beneficial effects that the present invention provides an ultrasonic beam forming method by using a neural network model and a specified neural network model. After the RF signal is received, the RF signal enters the neural network model for optimization processing. Target feature are extracted from convolution processing and pooling processing, so that an ultrasonic beam with better quality is obtained. In addition, by using the method, the calculation complexity is reduced, the development difficulty is also reduced, and costs for research & development is decreased.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A ultrasonic beam forming method based on a neural network model, the method being applicable to the signal processing during ultrasonic scanning, a processing device being connected to a receiver which is configured to receive ultrasonic echo radio frequency signal, wherein the ultrasonic echo radio frequency signal is processed by the neural network model so that the ultrasonic echo radio frequency signal forms an ultrasonic beam, the neural network model is built in the processing device, wherein the method further comprises the steps of:

Step S1, receiving, by the processing device, the ultrasonic echo radio frequency signal, and performing a preliminary processing of the ultrasonic echo radio frequency signal, so that the ultrasonic echo radio frequency signal is applicable to the neural network model;

Step S2, inputting, by the processing device, the ultrasonic echo radio frequency signal which has been subjected to the preliminary processing, into the neural network model;

Step S3, performing, by the neural network model, a convolution processing on the ultrasonic echo radio frequency signal which has been subjected to the preliminary processing for multiple times, and performing pooling processing after each convolution processing;

Step S4, flattening, by the neural network model, the three-dimensional data obtained from the last pooling processing, so as to convert the three-dimensional data into one-dimensional data;

Step S5, classifying, by the neural network model, the one-dimensional data for multiple times; and Step S6, performing, by the neural network model, grayscale mapping on the classified data to form the ultrasonic beam;

Step S3 comprises:

Step S31, performing a first convolution processing on the ultrasonic echo radio frequency signal, and outputting the ultrasonic echo radio frequency signal through a first activation function after the first convolution processing is completed, to perform a first pooling processing;

Step S32, performing a second convolution processing on the ultrasonic echo radio frequency signal which has been subjected to the first pooling processing, and outputting the ultrasonic echo radio frequency signal through a second activation function after the second convolution processing is completed, to perform a second pooling processing;

Step S33, performing a third convolution processing on the ultrasonic echo radio frequency signal which has been subjected to the second pooling processing, and outputting the ultrasonic echo radio frequency signal through a third activation function after the third convolution is completed, to perform a third pooling operation;

Step S34, performing a fourth convolution processing on the ultrasonic echo radio frequency signal which has been subjected to the third pooling processing, and outputting the ultrasonic echo radio frequency signal through a fourth activation function after the fourth convolution processing is completed, to perform a fourth pooling processing; and Step S35, performing a fifth convolution processing on the ultrasonic echo radio frequency signal which has been subjected to the fourth pooling processing, and outputting the ultrasonic echo radio frequency signal through a fifth activation function after the fifth convolution processing is completed, to perform a fifth pooling processing;

wherein all of the second pooling operation, the third pooling operation, the fourth pooling operation, and the fifth pooling operation are carried out by using an equalization processing method.

2. The ultrasonic beam forming method of claim 1, wherein Step S1 comprises:

Step S11, classifying the ultrasonic echo radio frequency signal based on the dimensional size thereof; and Step S12, converting one-dimensional grayscale image data obtained in Step S11 into three-dimensional color image data, and going to Step S2 thereafter.

3. The ultrasonic beam forming method of claim 1, wherein in Step S31, the first pooling processing is carried out by using a maximization processing method.

4. The ultrasonic beam forming method of claim 1, wherein Step S5 comprises:
Step S51, performing a first-level classification processing on the one-dimensional data, and outputting the classified one-dimensional data through a sixth activation function; and
Step S52, performing a second-level classification processing on the output data obtained in Step S51, and outputting the classified output data through a seventh activation function.

5. The ultrasonic beam forming method of claim 1, wherein the first activation function, the second activation function, the third activation function, the fourth activation function, the fifth activation function, and the sixth activation function are RELU functions, and the seventh activation function is a Softmax function.

6. The ultrasonic beam forming method of claim 1, wherein the neural network model, comprising:
an input layer for receiving an ultrasonic echo radio frequency signal;
a plurality of convolutional layers, wherein the first-level convolutional layer is connected to the input layer;
a plurality of pooling layers, wherein each of the plurality of pooling layers is connected to a corresponding convolutional layer, each convolution processing is followed by a pooling processing;
a smoothing layer, connected to the last-level pooling layer, flattening the three-dimensional data which has been subjected to the last pooling processing, so as to convert the tree-dimensional data into one-dimensional data;
a plurality of fully connected layers, the first-level fully connected layer is connected to the smoothing layer to classify the one-dimensional data for multiple times, and performing grayscale mapping on the classified data to form the ultrasonic beam.

7. The ultrasonic beam forming method of claim 6, wherein the plurality of convolutional layers comprise five convolutional layers, the plurality of pooling layers comprise five pooling layers, data obtained from a first convolutional layer is processed by a first activation function and is output to a first pooling layer for performing a maximization pooling; data obtained from the first pooling layer enters a second convolutional layer, data obtained from the second convolutional layer is processed by a second activation function and is output to a second pooling layer for performing equalization pooling, data obtained from the second pooling layer enters a third convolutional layer, data obtained from the third convolutional layer is processed by a third activation function and is output to a third pooling layer for performing equalization pooling, data obtained from the third pooling layer enters a fourth convolutional layer, data obtained from the fourth convolutional layer is processed by a fourth activation function and is output to a fourth pooling layer for performing equalization pooling, data obtained from the fourth pooling layer enters a fifth convolutional layer, and data obtained from the fifth convolutional layer is processed by a fifth activation function and is output to a fifth pooling layer for performing equalization pooling.

8. The ultrasonic beam forming method of claim 7, wherein the plurality of fully connected layers comprise two fully connected layers, including a first fully connected layer and a second fully connected layer, wherein the first fully connected layer perform a first compression and classification processing on the one-dimensional data, the compressed and classified one-dimensional data is output to the second fully connected layer through a sixth activation function, then the second fully connected layer performs a second compression and classification processing on the output data, the output of the second fully connected layer is processed by a seventh activation function and then output.

9. The ultrasonic beam forming method of claim 8, wherein the first activation function, the second activation function, the third activation function, the fourth activation function, the fifth activation function, and the sixth activation function are RELU functions, and the seventh activation function is a Softmax function.

\* \* \* \* \*